United States Patent [19]

Swank et al.

[11] 4,073,723
[45] Feb. 14, 1978

[54] ANTI-COAGULATING AND FILTERING BLOOD

[76] Inventors: Roy L. Swank, 2211 S.W. 1st, Portland, Oreg. 97201; David Danon, 16 Henkin St., Rehovot, Israel

[21] Appl. No.: 741,553

[22] Filed: Nov. 15, 1976

[51] Int. Cl.$^2$ .............................................. B01D 13/00
[52] U.S. Cl. .............................. 210/23 R; 128/214 R; 210/DIG. 23; 424/183
[58] Field of Search ............ 210/491, 321, 500, 23 R, 210/DIG. 23; 424/183; 128/214 R

[56] References Cited

U.S. PATENT DOCUMENTS

| 3,462,361 | 8/1969 | Greenwalt et al. | 210/500 R X |
| 3,593,854 | 7/1971 | Swank | 210/491 X |
| 3,673,612 | 7/1972 | Merrill et al. | 210/321 X |

OTHER PUBLICATIONS

Sanders, "Artificial organs," from *C & EN*, Apr. 5, 1971, pp. 32–49.

*Primary Examiner*—Frank A. Spear, Jr.
*Attorney, Agent, or Firm*—Eugene D. Farley

[57] ABSTRACT

Blood is passed through a heparin coated mass of filamentous polyester resin, polyamide resin, polyacrylic resin, glass, steel, cotton or cellulose. Thereafter the blood is passed through a mass of the same filamentous material which is not heparin coated, for removal of its content of leucocytes and platelets preliminary to blood bank storage and/or use in transfusions. Passage of the blood through the heparin-coated filamentous resin in the first step prevents the blood from coagulating in the second step.

The apparatus employed for the treatment comprises a vessel having an inlet with means for connection to a source of untreated blood; an outlet with means for connection to a receiving vessel; and a packing comprising at least one filamentous material of the group listed above. The packing comprises an upstream portion comprising heparinized filamentous material and a downstream portion comprising filamentous packing material substantially free from heparin. The upstream heparinized portion prevents the blood from coagulating while passing through the downstream unheparinized packing portion which thereupon removes the leucocytes and platelets from the blood.

23 Claims, 2 Drawing Figures

ANTI-COAGULATING AND FILTERING BLOOD

BACKGROUND AND GENERAL STATEMENT OF THE INVENTION

This invention pertains to method and apparatus for treating blood. It pertains particularly to method and apparatus for use in treating blood bank and transfusion blood for the removal of leucocytes and platelets.

It has been well established that the platelets and leucocytes contained in blood stored in a blood bank, and transfusion blood, tend to aggregate during storage and form masses having diameters of up to about 160 microns. The transfusion of blood containing such aggregates causes physiological and pathological changes in the lungs and other tissues of the patient's body. In some instances these changes result in serious complications.

For example, the leucocytes that are introduced into a body repeatedly by multiple transfusions have a tendency to induce immunological complications. Also, in cases of depressed immunological capacity transfusion of leucocytes may produce a graft vs. host reaction.

Swank, U.S. Pat. Nos. 3,448,041 and 3,593,854 disclose method and apparatus for the selective removal of leucocyte and platelet aggregates by passing the stored blood through a filter comprising filamentous materials such as filamentous polyester resin, filamentous polyamide resin, filamentous polyacrylic resin, filamentous glass, cotton and the like. Passage of the blood through these materials at the time of transfusion removes the harmful aggregates substantially completely without harming the other blood constituents. The patient thus is spared the harmful effects which he otherwise would suffer.

The Swank process accordingly increases the efficiency with which the blood bank blood routine may be carried out, since it enables the practice of a procedure broadly comprising withdrawing blood from a donor and passing the blood through a plastic tube into a plastic bag or other container which contains sufficient anti-coagulant to prevent the blood in the bag from coagulating. Where the bag has a capacity of 500 ccs, the volume of anticoagulant is about 50 ccs. The anticoagulant is in a solution in an isotonic and buffered solution calculated to prevent damage to the blood cells. Formerly the anticoagulant used was acid-citrate-dextrose (anticoagulant citrate dextrose solution, United States Pharmocopoeia XIX, p. 33); more recently, citrate-phosphate-dextrose (anticoagulant citrate phosphate dextrose solution, United States Pharmocopoeia XIX, p. 34).

After storage, the blood is passed through the filamentous filter described in the Swank patents aforesaid and introduced into the patient. Successful transfusions can be accomplished in this manner even after long storage periods. Also, the filter may be employed to great advantage as an extracorporeal filter during open heart surgery.

In view of the foregoing, the concept has arisen of removing the platelets and leucocytes from the blood in the first instance, before storage, rather than after storage. This technique would give rise to two advantages:

First, since the platelets and leucocytes are removed before storage, they cannot aggregate during storage, thereby simplifying the transfusion routine.

In the second place, it has been found that the lysosomes of leucocytes and platelets contain lytic enzymes which are released from platelet and leucocyte aggregates. These enzymes have the capacity and property of adversely affecting cells and tissues, thereby deteriorating the quality of the blood to be transfused. (Reid S. Connell and Roy L. Swank: Pulmonary microembolism after blood transfusions; an electron microscopic study, Annals of Surgery, Vol. 177, p. 40, 1973; and R. S. Connell, R. L. Swank, and M. C. Webb: The development of pulmonary ultrastructural lesions during hemorrhagic shock. J. of Trauma, Vol. 15, p. 116, 1975.)

This desirable result, i.e. the removal of the leucocytes and platelets from the blood prior to storage, is difficult of achievement, however, because if it is attempted to remove the leucocytes and platelets from the raw blood by passing the blood through a filamentous filter of the class referred to above in the Swank patents, the blood clots in the filter, making the filtration impossible.

It accordingly is the general purpose of the present invention to provide method and apparatus for removing leucocytes and platelets from blood without coagulation of the blood, providing a blood product suitable for storage over long periods of time, and suitable for use in transfusions of all categories.

The foregoing and other objects of this invention are achieved by the provision of a method which relies for its success upon the discovery that the blood anticoagulant heparin may be adsorbed efficiently on the filamentous filter materials aforesaid while retaining its anticoagulant properties over a substantial period of time.

In its broad outline the hereindescribed blood treating process accordingly comprises passing blood through a heparin-coated mass of filamentous polyester resin, polyamide resin, polyacrylic resin, glass, steel, cotton or cellulose. Thereafter the anticoagulated blood is passed through a mass of the same filamentous materials, but in a substantially heparin-free condition, for removal of its content of leucocytes and platelets preliminary to blood bank storage and/or use in transfusions.

The apparatus employed for the treatment comprises a vessel having an inlet with means for connection to a source of untreated blood, an outlet with means for connection to a receiving vessel, and a packing comprising at least one filamentous material of the group listed above. Preferably the packing comprises an upstream portion comprising heparinized filamentous material and a downstream portion comprising filamentous packing material substantially free from heparin. The upstream heparinized portion anticoagulates the blood so that it does not coagulate while passing through the downstream unheparinized packing portion which removes leucocytes and platelets from the transfusion blood.

DESCRIPTION OF A PREFERRED EMBODIMENT OF THE INVENTION

The invention is described herein with particular reference to the drawings wherein.

Figure 1:
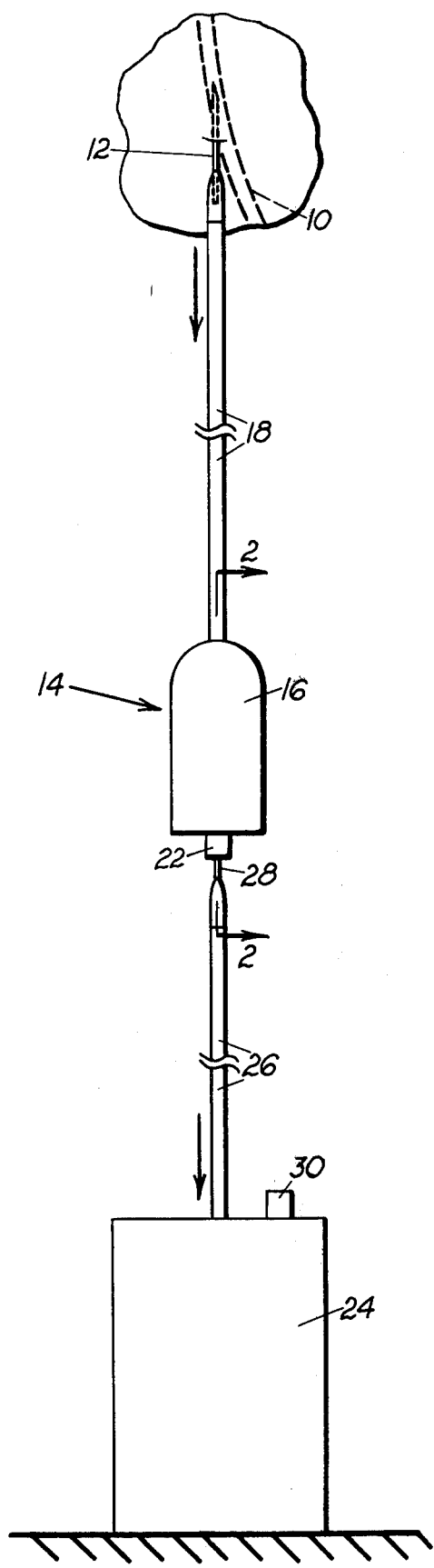
FIG. 1 is a schematic view of the apparatus used in the hereindescribed blood treating method for withdrawing blood from the vein of a donor, treating it, and transferring it to a blood bank storage container.
Figure 2:
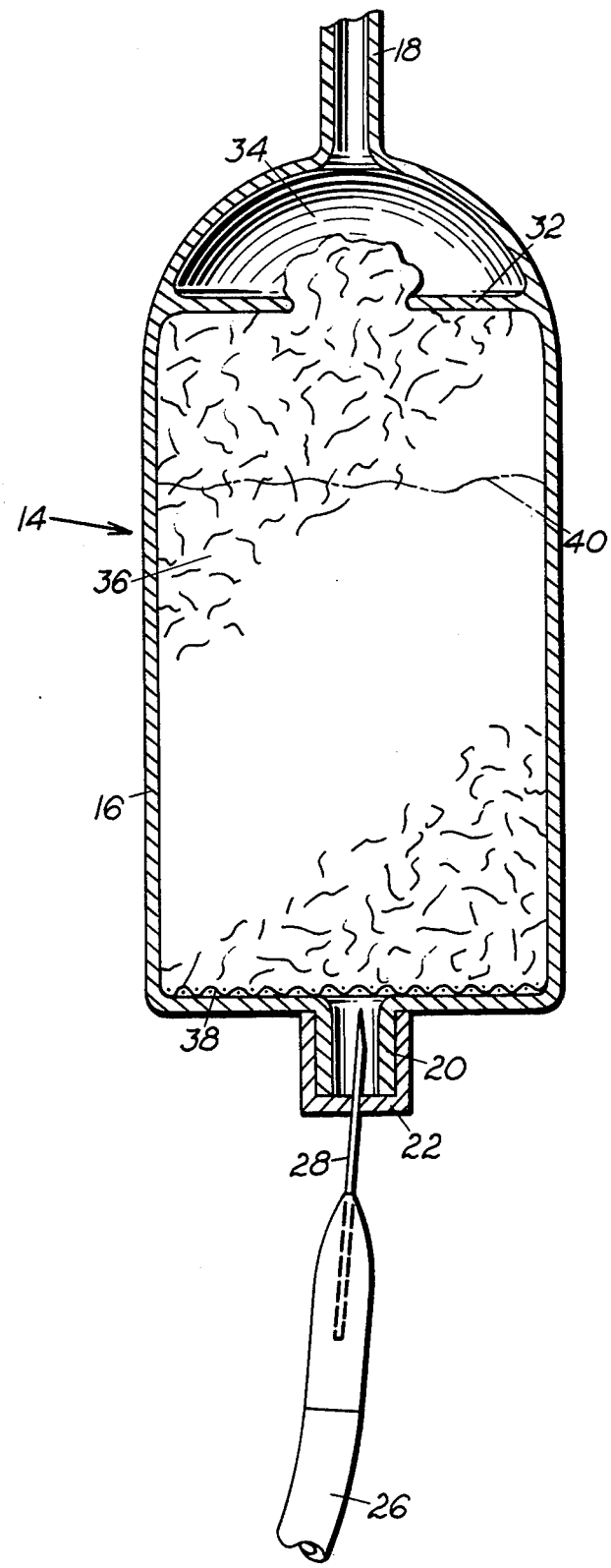
FIG. 2 is a longitudinal sectional view through the blood treating apparatus of the invention taken along line 2—2 of FIG. 1.

As illustrated in FIG. 1, in the practice of the hereindescribed invention blood is withdrawn from the vein 10 of a donor by inserting in the vein the needle 12 which is an integral part of the treating apparatus indicated generally at 14.

The apparatus includes a vessel 16 provided with blood inlet means associated with an infeed tube 18 which terminates with needle 12.

Vessel 16 also is provided with a discharge opening 20 closed off with a penetratable rubber cap 22, or other convenient means by which the conduit can be connected to the blood storage container.

The treating vessel is adapted for use with a conventional blood storage bag illustrated schematically at 24 having an infeed tube 26 with associated needle 28 and a discharge opening 30. Blood thus is withdrawn from vein 10 and travels via tube 18 through treating vessel 14 and out through tube 26 into storage bag 24.

While passing through treating vessel 14, the blood is subjected to two sequential treatments: In the first, it is anti-coagulated by heparinization so that it will not coagulate during the second stage of the treatment. In the second stage, the leucocytes and platelets are removed from the blood so that the blood leaving the treatment vessel and discharged into storage bag 24 is practically free from these components and remains so during subsequent storage and transfusion.

Treating vessel 14 preferably is compartmented. It can be divided by apertured partition 32 into an upper chamber 34 and a lower chamber 36.

Upper chamber 34 is substantially free of packing material or contains very loosely packed material and has for its function insuring that the packing material will not interfere with the flow of blood into and through the apparatus.

A screen 38 screens off discharge opening 20 so that the packing material will not be discharged from the apparatus together with the blood.

The packing material within the reaction vessel is of two categories: that above dashed line 40, consisting of from about 10 to 35% by weight of the total packing material, comprises heparinized packing material; the remainder below the dashed line 40, consisting of from about 65 to 90% by weight of the total packing material, comprises substantially unheparinized packing material.

In both cases, however, the packing material may have the same base: i.e., one or more members of the group of filamentous packing materials comprising filamentous polyester resins (Dacron and Kodel), filamentous polyamide resin (Nylon), filamentous polyacrylic resin (Orlon), glass wool, steel wool, cotton and cellulose (paper).

The filaments comprising the filamentous material should have lengths of not less than 100 microns and diameters of less than 60 microns, preferably less than 30 microns. Such filamentous materials are of sufficient size and character so that they will not pass through the filter and into the blood stream of the patient, or into the blood storage vessel. Also, they are sufficiently small in diameter that they provide a very large adsorption area so that the leucocytes and platelets and the aggregates thereof will adhere to them and will be removed from the blood.

The heparinized packing material contained in the upstream portion of the packing is prepared by soaking the fibrous material for from 5 to 15 minutes in a solution of from 0.02 to 0.2% by weight heparin in distilled water. The heparin employed is well known as a clinical anti-coagulant obtained from various pharmaceutical firms (anticoagulant heparin solution, United States Pharmacopoeia XIX, p. 35).

Under the foregoing conditions, from about 0.00025 to about 0.0025% heparin, dry weight basis, is coated on the fibrous material. This amount is important because too much heparin will destroy the adhesive qualities of the altered platelets so that they will not be removed by the fibrous packing material in the downstream portion of the packing. Then when the treated blood is introduced into the blood stream of a patient, the heparin will be washed off the altered platelets and harm to the patient may result.

After the soaking cycle has been completed, the excess heparin solution is removed by drainage and subsequent suction. The packing material then is dried at 20° to 24° C. in a flow of clean filtered air. In a typical case, the amount of heparin adsorbed to the fibers is approximately 700 international units per gram of fibers. This is slightly more than the minimum requirement for preventing coagulation of 500 U of blood.

The dry heparinized packing material then is inserted in the upstream portion of the treating vessel in an amount of from 10 to 25% of the total packing material. The remaining unheparinized or heparin-lean packing material then is placed in the downstream part of the reaction vessel and constitutes the remainder of the packing. A polyester or similar filter with a pore size of 100 to 170 microns is placed between the fibers and the bottom seal that incorporates the outlet.

In a typical instance, a cylindrical reaction vessel 12 cm. long and having a diameter of 3.8 cm. was packed one quarter full of heparinized packing material made by soaking Dacron wool for 10 minutes in a 0.1% by weight solution of heparin in distilled water, thereafter removing the excess heparin solution by suction and drying the heparin-impregnated wool with a stream of filtered air at room temperature.

Four grams of the resulting material in a finely fluffed condition was placed in the upstream end of the reaction vessel and 14 grams of the non-heparinized material was placed in the downstream portion thereof. Blood was passed through the packing at a transit time of about 12 minutes using a gravity flow of about 24 inches to 30 inches. The treated blood was passed into a 500 cc. blood storage bag containing anti-coagulant citrate-phosphate-dextrose solution. Its content of platelets was completely removed, and its content of leucocytes was reduced by about 95%.

Having thus described our invention in preferred embodiments, we claim as new:

1. The method of treating blood which comprises
   (a) soaking in an aqueous solution of heparin at least one filamentous material of the class consisting of filamentous polyester resin, polyamide resin, polyacrylic resin, glass, steel, cotton and cellulose,
   (b) draining the excess heparin solution from the filamentous material,
   (c) drying the filamentous material, whereby the dry heparin forms a coating on the surface of the filamentous material,
   (d) the heparin concentration of the aqueous solution and the soaking time of the filamentous material therein being chosen so that the amount of dry heparin coating is from about 0.00025 to about 0.0025 percent, dry weight basis,
   (e) and thereafter passing blood through a fluffed mass of a blood anti-coagulating quantity of said heparin-coated filamentous material at a rate to effect anti-coagulation of substantially all of said blood.

2. The method of claim 1 wherein the aqueous solution of heparin contains from 0.02 to 0.2% by weight heparin, and the soaking time is from about 5 to about 15 minutes, and including the step of air drying the heparin-treated filamentous material.

3. The method of claim 1 followed by the step of passing the anti-coagulated blood through at least one of the said filamentous materials in a heparin-lean condition for removing from the blood a substantial proportion of its leucocyte and platelet content.

4. The method of claim 3 wherein the filamentous material comprises polyester resin.

5. The method of claim 3 wherein the filamentous material comprises polyamide resin.

6. The method of claim 3 wherein the filamentous material comprises polyacrylic resin.

7. The method of claim 3 wherein the filamentous material comprises glass.

8. The method of claim 3 wherein the filamentous material comprises cotton.

9. The method of claim 3 wherein the filamentous material is comprised of filaments having average diameters of less than about 60 microns.

10. The method of claim 3 wherein the filamentous material is comprised of filaments having average diameters of less than about 30 microns.

11. The method of claim 3 including the step of mixing with the treated blood a blood bank storage quantity of anti-coagulant acid-citrate-dextrose solution.

12. The method of claim 3 including the step of mixing with the treated blood a blood bank storage quantity of anti-coagulant citrate-phosphate-dextrose solution.

13. The method of claim 3 wherein the filamentous material is coated with heparin by soaking it in an aqueous solution of heparin containing from about 0.02 to about 0.2% by weight heparin; and the heparin-coated filamentous material comprises from about 10 to about 35% by weight of the total quantity of filamentous material through which the blood is passed.

14. Apparatus for treating blood which comprises a vessel having an inlet with means for connecting to a source of blood to be treated, an outlet for evacuating treated blood, and a packing comprising a fluffed mass of at least one filamentous material of the class consisting of filamentous polyester resin, polyamide resin, polyacrylic resin, glass, steel, cotton and cellulose coated with from about 0.00025 to about 0.0025 percent by weight heparin, based on the air dry weight of the coated filamentous material.

15. The apparatus of claim 14 including downstream from the filamentous material a further quantity of at least one of said filamentous materials in a condition substantially free of heparin.

16. The apparatus of claim 15 wherein the filamentous material comprises polyester resin.

17. The apparatus of claim 15 wherein the filamentous material comprises polyamide resin.

18. The apparatus of claim 15 wherein the filamentous material comprises polyacrylic resin.

19. The apparatus of claim 15 wherein the filamentous material comprises glass.

20. The apparatus of claim 15 wherein the filamentous material comprises cotton.

21. The apparatus of claim 15 wherein the filamentous material is comprised of filaments having average diameters of less than 60 microns.

22. The apparatus of claim 15 wherein the filamentous material is comprised of filaments having average diameters of less than 30 microns.

23. The apparatus of claim 15 wherein the downstream heparin-free filamentous material comprises a quantity equal to from 90 to 75% by weight of the upstream heparinized filamentous material.

* * * * *